(12) United States Patent
Goldstein et al.

(10) Patent No.: US 8,305,575 B1
(45) Date of Patent: Nov. 6, 2012

(54) ADAPTIVE SPECTRAL SENSOR AND METHODS USING SAME

(75) Inventors: Neil Goldstein, Belmont, MA (US); Jason A. Cline, Burlington, MA (US); Pajo Vujkovic-Cvijin, Burlington, MA (US); Steven M. Adler-Golden, Newtonville, MA (US); Marsha J. Fox, Lexington, MA (US); Brian Gregor, Waltham, MA (US); Jamine Lee, Burlington, MA (US)

(73) Assignee: Spectral Sciences, Inc., Burlington, MA (US)

( * ) Notice: Subject to any disclaimer, the term of this patent is extended or adjusted under 35 U.S.C. 154(b) by 712 days.

(21) Appl. No.: 12/489,906

(22) Filed: Jun. 23, 2009

Related U.S. Application Data

(60) Provisional application No. 61/074,742, filed on Jun. 23, 2008.

(51) Int. Cl.
*G01J 3/28* (2006.01)
(52) U.S. Cl. ....................................... 356/326
(58) Field of Classification Search .................. 356/303; 382/162
See application file for complete search history.

(56) References Cited

U.S. PATENT DOCUMENTS

| | | | |
|---|---|---|---|
| 5,923,036 A | 7/1999 | Tague, Jr. et al. | |
| 6,128,077 A * | 10/2000 | Jovin et al. | 356/310 |
| 6,504,943 B1 | 1/2003 | Sweatt et al. | |
| 6,640,199 B1 | 10/2003 | Goldstein et al. | |
| 6,859,275 B2 | 2/2005 | Fateley et al. | |
| 6,996,292 B1 | 2/2006 | Gentry et al. | |
| 7,324,196 B2 | 1/2008 | Goldstein et al. | |

OTHER PUBLICATIONS

MacKentry, J.W., and the NGST-MOS Study Team, "NGST—MOS A Multi-Object Spectrometer using Micro Mirror Arrays Final Report of the NGST-MOS Pre-Phase A Science Instrument Study of the NGST Project" Final Report NASA Contract NAS5-98167 (1999).

Goldstein, Neil, et al., Thermal Infrared Spectral Imager with Programmable Spatial and Spectral Resolution and Hardware-based Implementation of Detection Algorithms, Jun. 24, 2008.

* cited by examiner

*Primary Examiner* — Tarifur Chowdhury
*Assistant Examiner* — Abdullahi Nur
(74) *Attorney, Agent, or Firm* — Brian M. Dingman; Mirick, O'Connell, DeMallie & Lougee, LLP

(57) ABSTRACT

An adaptive spectral sensor, and methods of using the sensor. The sensor uses a programmable band pass transmission filter to produce both contrast signals, which discriminate specific target materials from background materials by comparing spectral signatures in hardware, and scene radiance spectra. The adaptive spectral sensor may measure one or more scene spectra and may form a spectral image. The sensor may automatically adjust to changing spectral, spatial and temporal conditions in the environment being monitored, by changing sensor resolution in those dimensions and by changing the detection band pass. The programmable band pass can be changed on-the-fly in real time to implement a variety of detection techniques in hardware or measure the spatial or spectral signatures of specific materials and scenes.

29 Claims, 12 Drawing Sheets

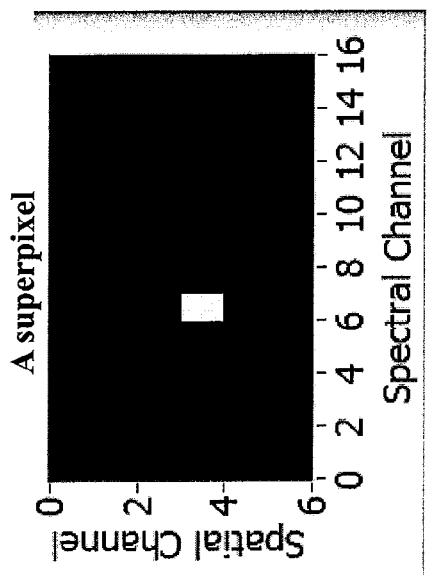
Figure 4A
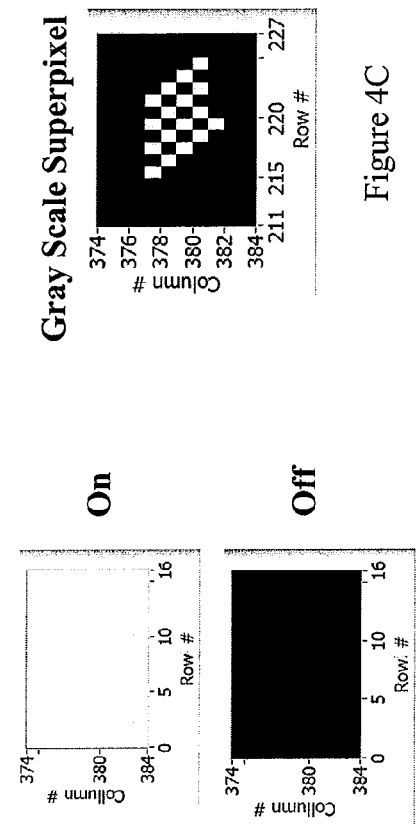
Figure 4C
Figure 4B

ADAPTIVE SPECTRAL SENSOR AND METHODS USING SAME

CROSS-REFERENCE TO RELATED APPLICATION

This application claims priority of Provisional application Ser. No. 61/074,742 filed on Jun. 23, 2008. The disclosure of the Provisional application is incorporated by reference herein.

STATEMENT REGARDING FEDERALLY SPONSORED RESEARCH

This invention was made with government support under the following contracts: Chemical/Biological Agent Standoff Detection, Contract No. HDTRA1-05-P-0126 (DTRA), Fast Adaptive Spectrometer Programmable for the Evaluation of Combustion (FASPEC), Contract No. W31PQ-05-C-R095 (Army), and Infrared Derivative Spectroscopy for Open Path Sensing, Contract No. W911SR-05-P-0063 (Army). The government has certain rights in this invention.

FIELD OF INVENTION

This invention relates to an adaptive spectral sensor that uses a programmable band pass transmission filter to produce both contrast signals, which discriminate specific target materials from background materials by comparing spectral signatures in hardware, and scene radiance spectra.

BACKGROUND OF INVENTION

The current invention exploits a class of devices that produce spatially and/or spectrally encoded imagery or point signals by first dispersing the light from a distant scene, encoding the light using a mask that selects specific combinations of wavelengths and/or spatial positions, and then recombining the light on a detector that records the encoded polychromatic signal. Such devices often make use of a programmable spatial light modulator to create a signal-encoding mask. The programmable modulator provides the ability to encode arbitrary spatial or spectral patterns on each resolution element, and vary those patterns temporally. The patterns can be used to generate specific and highly complex spatial or spectral band passes on an image. Spectra can then be obtained by cycling the system through a sequence of spectral band passes. Spatial imagery can be obtained by encoding for different spatial elements of the dispersed image, and collected either temporally on a point detector, or simultaneously with a detector array.

Examples of such signal encoders are described in Goldstein et al. (U.S. Pat. No. 7,324,196), which describes three hardware implementations using a single point detector or detector array along with a digital micromirror device (DMD) to provide addressable spatial and spectral band selection. Sweatt et al. (U.S. Pat. No. 6,504,943) employ an input slit and linear array detectors to encode a spectral pass band on a pair of one-dimensional images. Tague (U.S. Pat. No. 5,923,036), MacKentry (1999) [MacKentry, J. W. and the NGST-MOS Study Team. "NGST-MOS A Multi-Object Spectrometer using Micro Mirror Arrays Final Report of the NGST-MOS Pre-Phase A Science Instrument Study of the NGST Project" Final Report NASA contract NAS5-98167 (1999)], Gentry (U.S. Pat. No. 6,996,292), and Fateley (U.S. Pat. No. 6,859,275) teach methods of spatial-spectral imaging in which a spatial light modulator is used to define the input slit of a spectrograph, allowing either a single detector spectrograph or a one-dimensional imaging spectrograph to select different spatial elements of an input image for spectral analysis. Fateley (U.S. Pat. No. 6,859,275) also teaches a wide variety of devices using spatial-spectral information processing.

Many of the above-mentioned signal encoders can be used to perform spatial or spectral processing in hardware. This ability, which is often referred to as compressed sensing, allows the direct measurement of a spectral contrast signal, which relates to the level of target detection confidence, with optimum duty cycle. Goldstein et al teaches the application of a spectral template designed to identify a spectral feature that is characteristic of a specific object, liquid, gas, or scene condition. Sweatt et al. teaches the application of a wide variety of analog spectral filter functions using a DMD device and dividing the light between two detection legs, each with an independently controlled amplitude modulator. Both patents are specific to applications of a defined hardware configuration. Sweatt et al. teaches the application of a variety of analog filters, including matched filters, spectral basis functions, and projection operators, by applying the positive part of the filter function to one detection leg, and the negative part of the filter function to another detection leg. The current invention allows the implementation of any analog filter, using a single detection leg and using the spatial light modulator to perform both spatial selection and amplitude modulation.

SUMMARY OF INVENTION

The current invention addresses a system and method for exploiting a variety of hardware embodiments of a spectral or spatial encoder, including those with only one detection leg, to produce contrast signals, including contrast imagery, contrast spectra, and spectrally resolved imagery using encoder masks that implement spatial and spectral filters that are tailored to a specific sensing application. Applications might include signature measurement, target detection, quantification, and discrimination. The invention includes the ability to refine the encoder masks used to implement the filters in real time to adjust to different detection tasks and evolving target and background conditions. This ability to update the encoding masks for evolving backgrounds is critical for accurate assessment of the target characteristics.

The system can operate in different, software selectable modes, including 1) hyperspectral imaging with user selected spatial and spectral resolution, 2) contrast imaging with a mission-specific spectral template or matched filter, and 3) spatial contrast sensing using a spatial template or matched filter to discriminate for spectra of objects in a particular spatial class. The system can shift between modes on a sub-second time scale, to perform a combination of functions. For example, periodic spectral image scans can be conducted to determine the evolving spectral characteristics of the background scene. Such contemporaneous data, and/or a priori data, can then be combined with the known target spectra to produce optimal templates for detection of the target in the presence of the background.

The system can also cycle through encoded masks designed to detect different aspects of the target. For example, the target temperature can be determined using a set of target spectral filters with different temperature dependence. Alternatively, the abundance ratio of two different targets can be measured with two different spectral filters. Furthermore, the system can isolate spectra of an object of a particular size, or of moving objects using spatial discriminants. In each case, the encoding masks can be tailored to measure the desired property of a target or analyte located within the scene with minimal interference from background objects Spatial imagery can be developed by sequentially cycling through masks that encode different spatial regions of the dispersed image. Thus, spatially resolved spectral imagery can be produced using a single detector element.

The invention can exploit time-domain multiplexing to produce the spectral contrast imagery and spectrally resolved imagery. In spectral contrast imagery, the system can cycle rapidly through two or more spectral filters and process the signals to produce a spectral contrast image.

The adaptive spectral imager can be used to perform, in hardware, any detection method that is based on linear operations of observed spectra. The overall effect of applying the spectral filter is to perform a projection operation. In other words, the detector measures the inner product (dot product) of the spectral filter with the scene spectrum. Any and all detection algorithms based on linear combinations of spectral features, including spectral scans, matched filters, sub-space projection, principal component analysis, linear anomaly detection, and derivative detection, can be implemented using a combination of spectral filters, and can be implemented in the adaptive spectral sensor. This ability can be thought of as optical computing using adaptable analog filters.

Similarly, spatial filters can be used to implement a pattern recognition task, or to produce complete spectral imagery.

This invention also includes the implementation of analog filters through the use of grayscales formed on the encoder to provide variable attenuation in specific spatial and spectral bands. Such variable attenuation allows the construction of the analog spectral filters used to implement detection algorithms. A single positive-valued analog filter function can be applied with a single mask to allow continuous imaging with the selected spectral response. Alternatively, a filter encompassing both positive and negative values can be applied using a series of two masks, one for the positive parts of the filter function, and one for the negative parts of the filter function, the data from the two masks are subtracted to form a contrast image with the applied filter function. The use of sequential masks is a useful feature that is required by many detection systems based on AC-coupled detectors. For example, most infrared detectors are AC-coupled and must use chopping to produce an AC signal. The subtraction of the alternate masks accomplishes both chopping and the application of the filter function in one step.

The grayscales can be applied using either spatial or temporal multiplexing. In spatial multiplexing, each spatial and spectral resolution element consists of a group of addressable modulator elements on the spatial light modulator. The grayscale is implemented by turning a fraction of the modulators on, while leaving the rest off. In temporal multiplexing, the modulator elements are turned on and off using pulse-width modulation to produce a time-averaged attenuation.

This invention also includes a number of physical embodiments of encoders for use in an adaptive spectral sensor. One such embodiment, which utilizes a single detector, provides one-dimensional or two-dimensional spatial imagery with a programmable spectral bandpass. This makes a convenient, and low cost platform for adaptive spectral imagery. It is particularly useful for operation in the infrared spectral regions in applications such as chemical detection, leak detection, and surface contamination monitoring. A second embodiment uses a concentric spectrograph, similar to those described in Goldstein et al. (U.S. Pat. No. 7,324,196) in conjunction with a detector array.

This invention features in one embodiment a method of detecting specific properties of a radiance image of a scene in hardware using a spectrally encoding sensor system comprising: a spectrograph that forms a dispersed image comprising multiple spectral components displaced along a dispersion direction; a programmable spatial mask for encoding filter functions on the dispersed image where the filter functions select specific spectral pass bands and/or spatial locations; and optical elements that direct the encoded dispersed radiation onto a detector that records the intensity transmitted through each mask. In this embodiment the method comprises successively encoding a series of two or more filter functions with the programmable spatial mask, to make two or more successive measurements that each measure the inner product of the filter function with the scene radiance spectrum, where the filter function contains a combination of spectral pass bands that emphasize one or more specific properties of a target or analyte that may be located within the scene, and comparing two or more measurements using linear operations such as subtraction and ratios, to produce a contrast signal indicative of the specific properties of the scene.

The filter functions can be analog transmission functions that are implemented using grayscales on the spatial mask. The filter functions can be adaptive filter functions that emphasize a known and pre-selected target spectrum while minimizing the response to other known spectral features within the scene. The method may further comprise automatically, dynamically adjusting the filter functions to reflect changes in the background spectral features within the scene. The adjustment may be based on knowledge of the general scene conditions. The monitored scene may be part of a process or system with a well defined range of possible spectral characteristics that depend on the state of the system or process. The process may involve hot combustion products and the physical properties may include temperature, concentrations, or dynamic fluctuations of combustion products. The physical property may be measured at a specific location within the field of view of the sensor. The method may further comprise using fiber-optics to direct radiation from a specific location to the sensor system. The method may further comprise recording the physical property as a function of time to determine the dynamic behavior of the system.

The specific property may comprise a concentration, temperature, or other physical property of a specific analyte within the scene. The specific property may comprise the relative values of the physical properties of two or more analytes. The method may further comprise producing a control signal proportional to the contrast signal that is used to initiate a physical action that affects the specific property. The filter function may be selected to produce the derivative of the target or analyte spectrum.

The spatial light modulator may be a digital micromirror array and the basic resolution unit may be a superpixel consisting of multiple individual mirrors; the spectral and spatial resolution of the measurement can in this case be adjusted by changing the size and shape of the superpixel. The grayscales may be implemented by activating a fraction of the individual mirrors within the superpixel element.

The grayscales can be implemented using variable on and off times for the individual mirrors. Two or more analog transmission functions can be used to implement a generalized version of a matched filter, or other detection methods based on linear projection operations, which optimizes signal to noise ratio in the presence of constant detector read noise. The analog transmission functions may be used to project the radiance spectrum onto a set of spectral basis functions representative of materials and conditions in the scene.

The method may further comprise collecting detailed spectral scans of the scene to determine the spectral features of the background scene. The method may further comprise updating the optimal filter functions for detection based on a spectral data recorded previously for the specific scene. The method may further comprise updating the optimal filter functions for detection based on the most recent spectral data collected over a range of viewing or operating conditions.

The method may further comprise recording the transmitted intensity through at least one spatial mask as a function of time to determine the dynamic behavior of the system. The filter function may comprise a spatial filter function to resolve spatial structure in the image. The method may further comprise a set of spectral filter functions that resolve the spectral information in the scene using a reduced number of spectral filters relative to a full spectral scan at constant resolution.

Featured in another embodiment is an adaptive spectral sensor comprising a spectrograph that forms a dispersed image comprising multiple spectral components displaced along a dispersion direction, a programmable spatial mask for encoding filter functions on the dispersed image where the filter functions select specific spectral pass bands and/or spatial locations, and optical elements that direct the encoded dispersed radiation onto a detector that records the intensity transmitted through each mask, and a processing and control system that produces a sequence of masks and processes the detected time-sequence signals to develop a one-dimensional spatially resolved image of a spectral contrast signal indicative of the specific properties of the scene.

The spectrograph may define an input slit and a single convex grating. The detector may have only a single element. Spatial resolution may be achieved through the sequence of spatial masks on the spatial light modulator. The spectrograph may define an input slit, in which case a full two-dimensional contrast image may be produced by making successive measurements with the spectrograph input slit in different positions. The time-dependence of the detected radiation transmitted through at least one spatial mask may be monitored in real-time to track the variations in a physical property within the scene.

Also featured is a method of detecting specific properties of a radiance image of a scene in hardware using a spectrally encoding sensor system comprising: a spectrograph that forms a dispersed image comprising multiple spectral components displaced along a dispersion direction; a programmable spatial mask for encoding filter functions on the dispersed image where the filter functions select specific spectral pass bands and/or spatial locations; and optical elements that direct the encoded dispersed radiation onto a detector that records the intensity transmitted through each mask. In this embodiment the method comprises applying information about the range of possible spectral features in the scene to develop a set of spectral filter functions that provide a near-complete description of all possible spectral features in the scene and allow the detection of high-resolution spectral information using a small number of measurements, the spectral filter functions designed for the detection of specific physical properties in the scene, encoding one or more spectral basis functions with the programmable spatial mask to measure the inner product of the filter function with the scene radiance spectrum, and producing a signal indicative of the specific physical property in the scene.

A spectrum of the scene may be measured by sequentially applying members of the set and comparing the measurements. The method may further comprise comparing two or more measurements using linear operations such as subtraction and ratios, to produce a contrast signal indicative of the specific properties of the scene.

Another embodiment features a method of detecting specific properties of a radiance image of a scene in hardware using a spectrally encoding sensor system comprising: a spectrograph that forms a dispersed image comprising multiple spectral components displaced along a dispersion direction; a programmable spatial mask for encoding filter functions on the dispersed image, where light from a single spatial element is directed to two or more distinct areas of the spatial mask, and where the filter functions select specific spectral pass bands; and optical elements that direct the encoded dispersed radiation onto a detector array that records the intensity transmitted through each distinct area of the spatial mask. In this embodiment the method comprises encoding two or more filter functions with the programmable spatial mask, to make two or more simultaneous measurements that each measure the inner product of a filter function with the radiance spectrum of the spatial element of the scene, where the filter functions each contain a combination of spectral pass bands that emphasize one or more specific properties of a target or analyte that may be located within the scene, and comparing two or more measurements using linear operations such as subtraction and ratios, to produce a contrast signal indicative of the specific properties of the scene.

BRIEF DESCRIPTION OF THE DRAWINGS

Other features and advantages will occur to those skilled in the art from the following description of the preferred embodiments and the accompanying drawings in which:

FIGS. 4A-4C show examples of superpixels according to an embodiment of the invention;

DETAILED DESCRIPTION OF EMBODIMENTS
OF THE INVENTION

Figure 1:
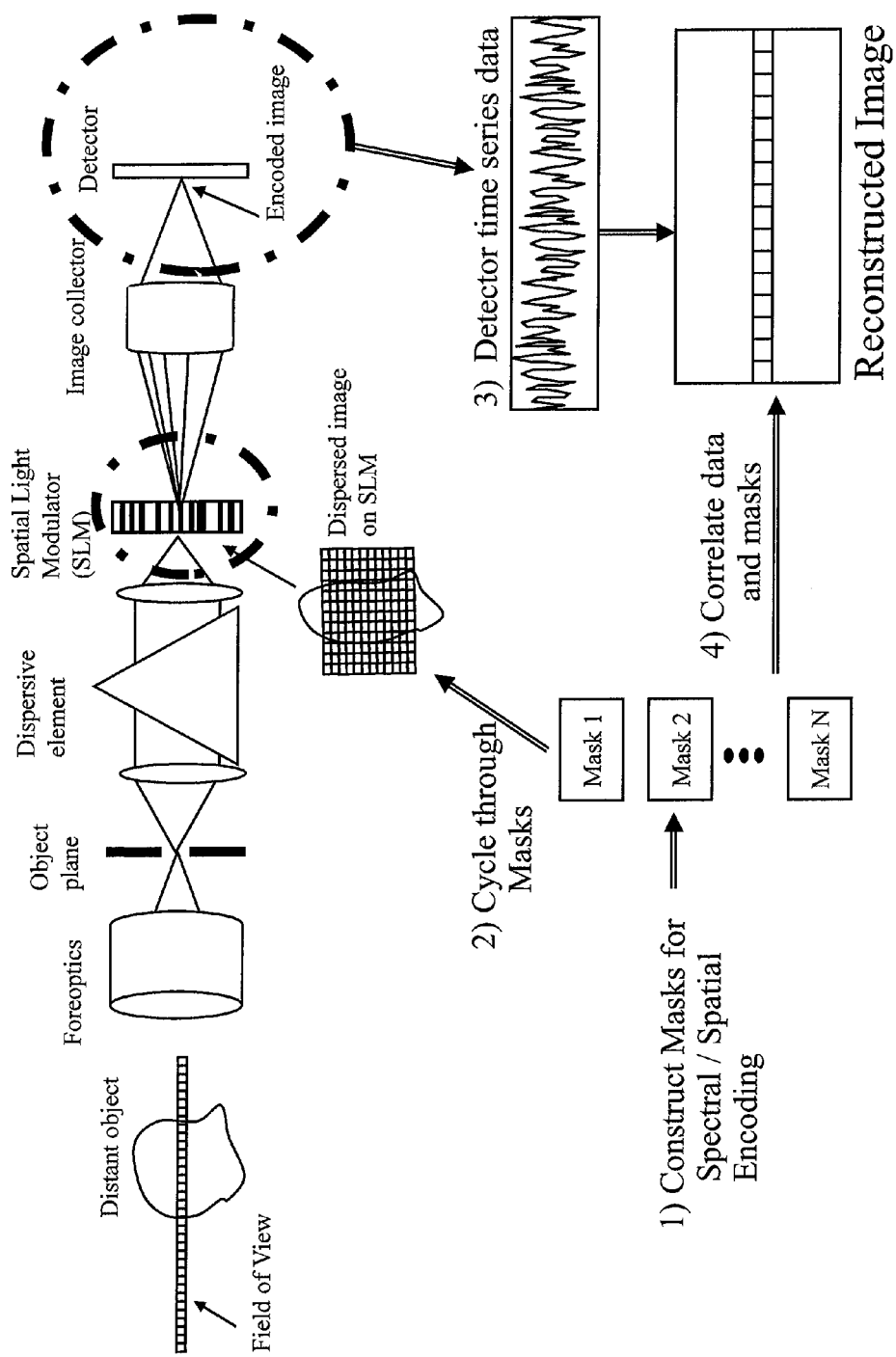
FIG. 1 is a schematic diagram of an adaptive spectral sensor according to an embodiment of the invention, the figure also broadly indicating the basic steps of a method of the invention.

FIG. 1 illustrates the basic concept of one embodiment of the inventive adaptive spectral sensor and the inventive methods. In this embodiment, the resulting image has one spatial and one spectral dimension. The adaptive sensor contains foreoptics to create an image of a distant target, a signal encoder, such as described in the Goldstein, Gentry, or Sweatt patents, and a control and data processing system. It contains a computer or other signal processing device along with peripherals for analog to digital conversion of the input signals and triggering the sequence of SLM masks, and means of loading the masks onto the SLM. The controller determines the type of filter function to apply, computes the filter function at the appropriate spatial and spatial resolution, produces a set of N spatially and spectrally encoded masks, cycles through the masks, collects the data from the optical detector, and processes the data to produce the reconstructed spectral image. The control system may also include means of adapting the sensor to accomplish different tasks and adapt the applied filter functions to adapt to evolving scene conditions or system requirements.

The inventive adaptive spectral sensor disperses the light and reimages onto a two-dimensional spatial light modulator (SLM), which blocks or attenuates specific spatial and spectral elements of the dispersed image and transmits others. The transmitted light is collected and reimaged onto a photodetector that produces an electrical signal proportional to the transmitted radiance. The photodetector may be a single element detector or an array detector.

Figure 2:
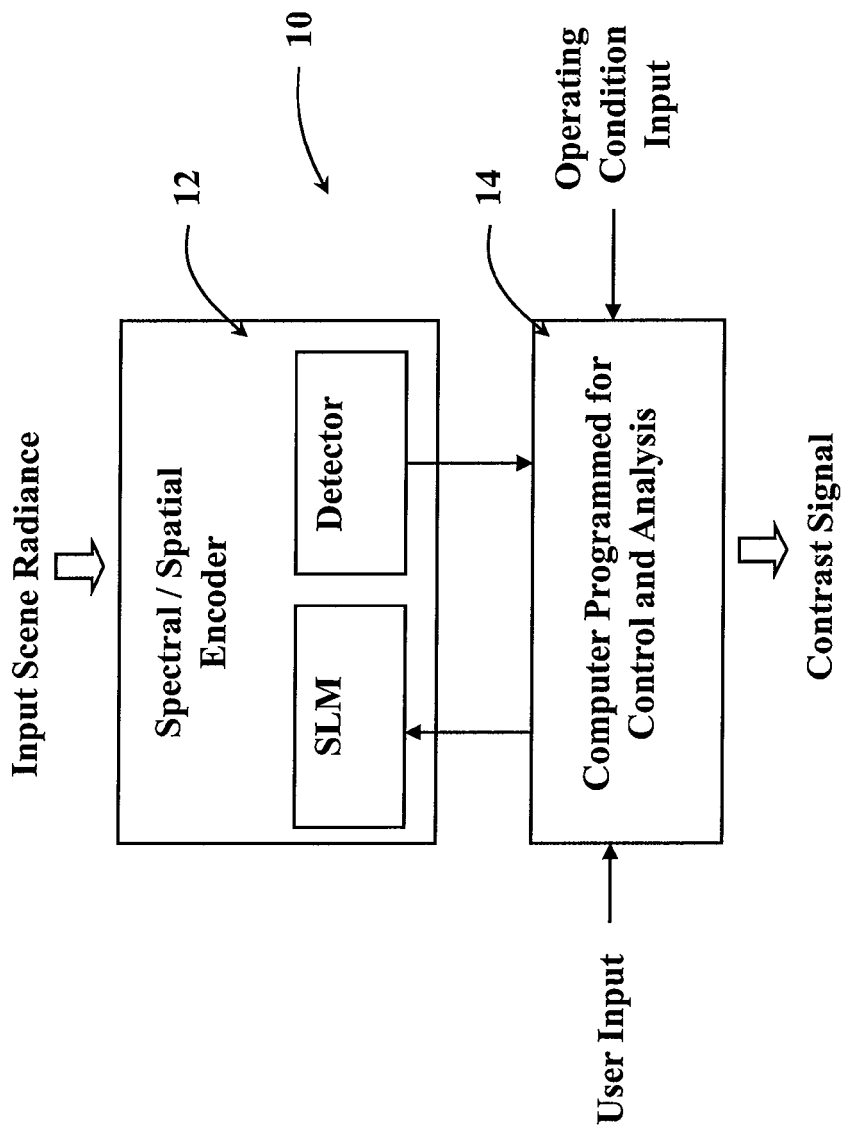
FIG. 2 is a simplified schematic diagram of a system for accomplishing the various embodiments of the invention.

FIG. 2 shows inventive system 10 comprising adaptive spectral/spatial encoder 12 and programmed computer 14. Control and analysis is accomplished by a programmed general purpose computer under appropriate user input such as through a keyboard and mouse, for example. Proper control is provided to the SLM, and the detector output is analyzed to create the contrast signal.

Figure 3:
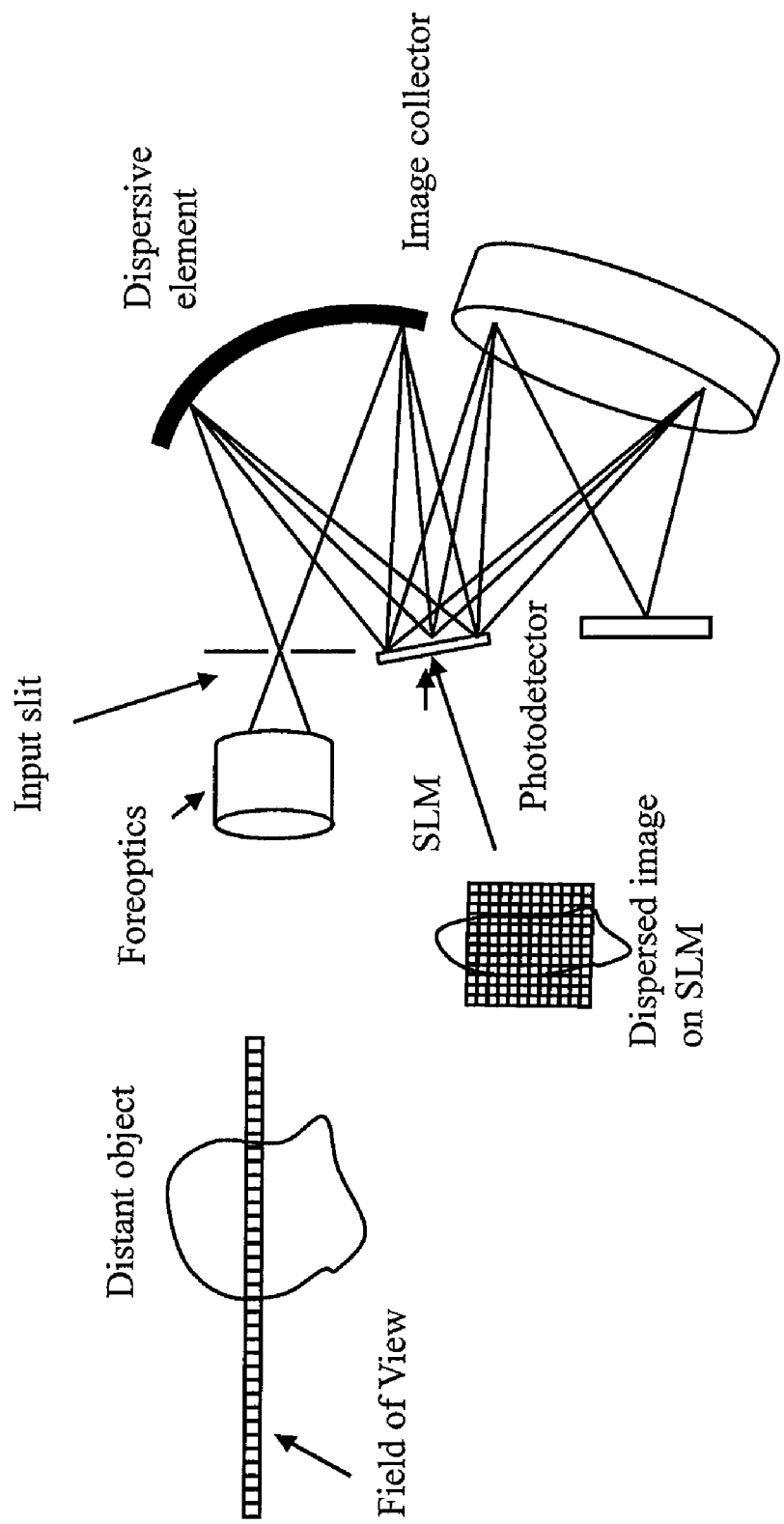
FIG. 3 is a conceptual layout of a single detector adaptive spectral sensor according to an embodiment of the invention.

FIG. 3 illustrates this process using a preferred embodiment of a spectral sensor for implementing the inventive adaptive sensing method. The embodiment includes a spectral sensor that uses a single detector element in conjunction with a slit and the SLM to encode spectral imagery. In this case, the spatial light modulator is a two-dimensional Digital Micromirror Device (DMD) consisting of an array of individually addressable mirrors. The image of the distant target is focused on an input slit, dispersed and reimaged to form a dispersed image on the DMD. One dimension of the image corresponds to the spatial location along the slit, while the other dimension corresponds to the wavelength of the dispersed light. A second spatial dimension can be obtained by temporally scanning the slit along the spectral dimension. The DMD mirrors are individually addressable, and can be tilted in one of two directions corresponding to "on" and "off". A collection optic collects the light reflected in the on direction and concentrates it on the detector.

Spectral imaging is preferably accomplished by grouping the DMD mirrors into 'superpixels' that define units of spatial and spectral resolution. The superpixel may be of arbitrary size, depending on the desired spatial and spectral resolution. Typically, the superpixel will be of order ten pixels wide in each dimension, and will contain tens or hundreds of individually addressable mirrors. Each mirror is inherently binary—either on or off. The superpixel transmission can be adjusted by turning on a fraction of the mirrors to produce a grayscale with a resolution of order one part in a hundred. The ability to change the size and content (binary or grayscale) of each superpixel enables the rapid adaptability of the device.

FIGS. 4A-4C illustrate binary and grayscale superpixels. FIG. 4A illustrates a single superpixel that defines the basic spatial and spectral resolution unit of a mask that is applied to the spatial light modulator. The mask is divided into a number of superpixels, some of which are turned on, and some of which are turned off. The rows of superpixels define a set of spectral channels. The columns of superpixels define spatial channels. Each of these superpixels are realized as a group of individual addressable mirrors on the SLM. For a binary superpixel, all of the mirrors are either turned on or off, FIG. 4B. Alternatively, the superpixel can be realized as a grayscale, where a subset of the mirrors are turned on, FIG. 4C.

The system and method of this invention includes a data processing and control system. The processing and control system has real-time data collection of the input signals, and generates the spatially and spectrally encoded masks required for real-time operation. The system allows multiple modes of operation, allowing the selection of spectral and spatial resolution, as well as the generation and application of spectral templates for producing the spectral or spatial contrast signals.

The data processing and control system may also have supervisory logic that allows it to change and adapt operating parameters and modes of operation on the fly, for example in response to measured changes in the target and background signals or operating conditions. Many detection techniques, including matched filters, sub-space projection, and anomaly detection, involve the generation of filters that maximize a quantity of interest, while minimizing the interference from the background. The filters are specific to a set of background conditions and may be based on data collected in situ. In many cases, it is ideal to optimize filters to account for the known conditions in a certain scene. The inventive system can periodically measure the properties of the background and adjust the filters accordingly.

For example, in a thermal infrared surveillance system, the backgrounds, consisting of partially-emissive materials with some reflectivity, may change in radiance as a function of temperature, illumination and time of day. The system may devote the bulk of its time to producing spectral contrast images of a scene, with the spectral templates set to identify a specific target. Some small fraction of time, say 1 second every minute, would be used to measure the full spectrum of the background. This background information would then be used to continuously update the spectral templates used for identification of the target.

Similarly, in airborne reconnaissance, the system may keep a record of background spectra observed in previous measurements of the same scene. This scene-specific background information, along with information on the illumination and time of day, can be used to update spectral templates used to detect targets against this background.

Similarly, in a process control monitor, or a combustion monitor, the background interference may be a known function of operating conditions. Data on operating conditions can be input to the system, which will adjust the spectral filters accordingly.

The invention may also include elements of a control system, in which an action is initiated in response to the conditions detected by the sensor. The action may include physical action, such as operating a valve, activating a switch, or pointing the sensor, and may include generation of an output signal useful for control. The output signal may be a proportional signal, such as a valve setting, or a binary signal, such as an alarm, or a signal to initiate a physical action.

Preferred Spectral Encoder Embodiments

One preferred embodiment of a spectral encoder for the invention is shown in FIG. 3. This embodiment is similar to an embodiment of Goldstein (U.S. Pat. No. 7,324,196), but has less stringent requirements for light collection, and enables two-dimensional imaging. The spectral encoder of FIG. 3 contains a single pass spectrograph, a spatial light modulator, and a collection optic that directs the light onto a detector. Light from a distant object is collected by foreoptics and forms an image at the object plane of the spectral encoder. A slit in the object plane defines a one-dimensional slice of the image. The spectrograph forms a dispersed image of the slit on the spatial light modulator. The Spatial Light Modulator (SLM), acting in conjunction with the slit, can be programmed to address specific spectral and spatial components of the image. Selecting a column of pixels along the dispersion axis selects a spectral pass band. Selecting a row of pixels along the perpendicular direction selects for a spatial location along the long axis of the field of view. The spatial light modulator selects spatial and spectral elements of the scene and directs them towards a collection optic, which combines the light onto a detector.

The spectrograph may consist of a single concave element that produces a focused, spectrally resolved image of the slit on the spatial light modulator. The concave element may be a torroidal grating that compensates for system astigmatism. The concave element may be holographic grating. Alternatively, the spectrograph may be a concentric spectrograph of the Dyson, or Offner type configurations.

The collection optic may include a dispersive element that reverses some, or all of the dispersion of the spectrograph. It may in fact use the same dispersive elements as the first spectrograph.

This invention in part differs from Goldstein et al. by the use of a slit in the object plane to define the field of view of the system and the use of a larger detector element that enables two-dimensional imagery and reduces the optical imaging requirements of the collection optic. The slit, in conjunction with the rows of the spatial light modulator, defines the wavelength of the system and the field of view. The collection optic, therefore need not make a well-formed monochromatic image on the detector, but merely must collect the light onto the element of the detector array.

In one implementation, the detector is a single element detector, which is large enough to collect light from the entire slit height. The DMA and slit are then used to perform one-dimensional spatial, spectral contrast imaging. Alternatively, the detector can be an array segmented into discrete spatial positions. Each spatial position is imaged onto an array element.

Two-dimensional imaging can be accomplished by moving the slit, or using a spatial light modulator to form an addressable slit. The spectral encoder can collect light over a range of slit positions, disperse it and collect the dispersed light onto the detector. The location of the slit in the object plane defines the spatial position in the second dimension. The rows of the SLM define the spatial location in the first dimension. The transmitted wavelength is determined by the slit position, in conjunction with the columns of the SLM. For each slit position, there is a unique set of spatial masks that produce the desired spectral contrast signal. The system can produce the same contrast signal for two different slit positions by applying a different set of masks with the same wavelength dependence.

The spectral encoder of the adaptive spectral sensor can be used in any wavelength range, including the infrared, visible, and ultraviolet portions of the spectrum.

In one implementation the invention uses an infrared detector and machined concave gratings to cover parts of the spectral range from 3-14 microns and is suitable for monitoring the thermal emission and absorption of materials of objects at ordinary ambient temperatures or temperatures somewhat above or below ambient temperatures. This system provides spatially resolved spectral contrast detection of objects in the environment or in process flows.

A second implementation uses an array of detectors and a concentric spectrograph to measure features in the 1-micron spectral region (0.2-2 microns), and is suitable for monitoring thermal emission and absorption of combustion sources at elevated temperatures in the 1000-4000 K range. This implementation may be used to make high-speed measurements of the physical properties of a combustion flow, such as the density of combustion products and the temperature of the combustion products. Each of the elements of the array detector corresponds to a single spatial input channel. They can be monitored simultaneously to give high-speed data at sample rates of order 100 kHz.

In one embodiment, fiber-optics are used to deliver the light from a distant scene to the spectral encoder. Multiple fibers can be used to image multiple spatial elements of the scene.

Spatial multiplexing may be used to view a single spatial element, or fiber, through multiple spectral filters. The image of the scene, or input fiber, may illuminate multiple rows of the spatial light modulator. Different spectral filters can be applied to different rows of superpixels on the SLM. These are then imaged onto different elements of the array detector to provide simultaneous measurement of the same object with two or more spectral filters.

Second Preferred Embodiments

Creation of Spectral Contrast Imagery

Spectral images are preferably constructed by changing the transmission of the individual superpixels and collecting the resultant signals. This is done using time-domain multiplexing and a series of encoder masks, each with a defined attenuation for every superpixel. The system cycles through the masks in rapid succession, records the transmitted radiance, and then processes the data to reconstruct spectra or a spectral image. This spectral image may be either a full spectral image, or a spectral contrast image.

Figure 5A:
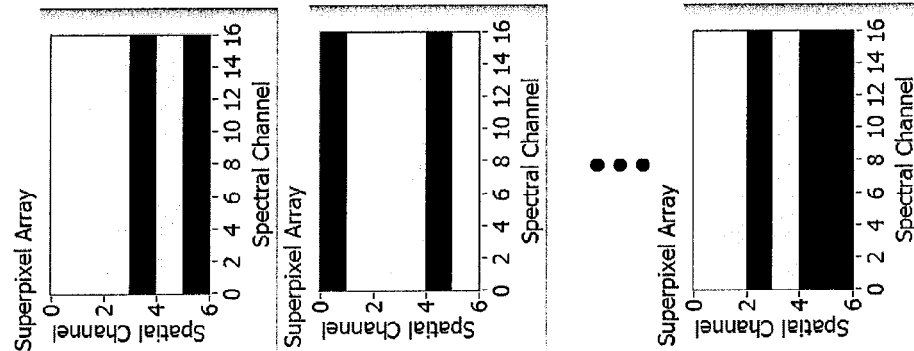
FIG. 5A illustrates an example of encoding the spatial dimension as a set of transform masks according to an embodiment of the invention.
Figure 5A:
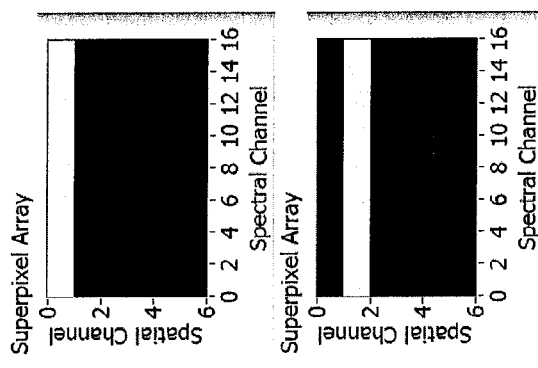
Figure 5B:
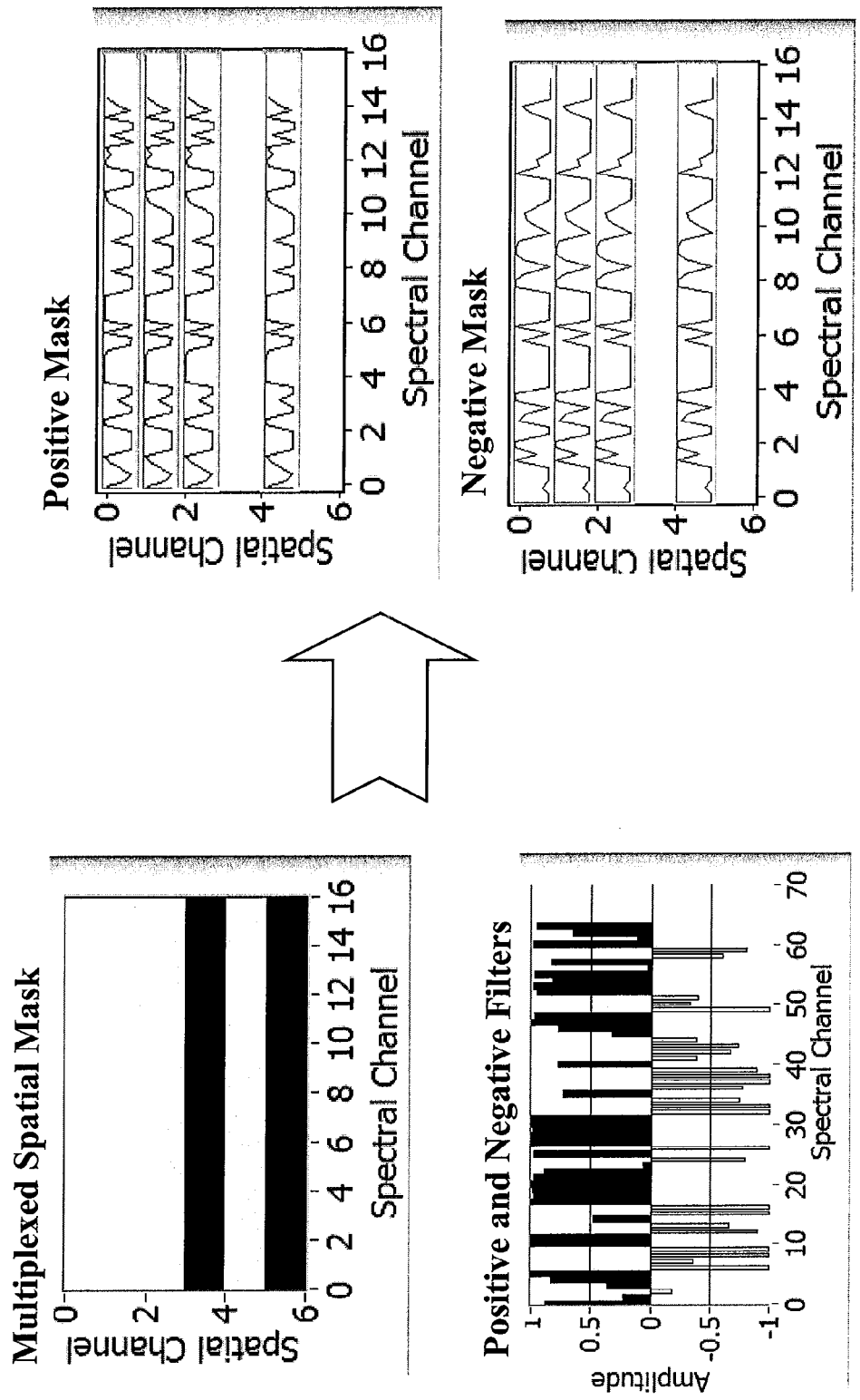
FIG. 5B illustrates a process of spectrally encoding a single spatial mask using two encoder masks according to an embodiment of the invention.
Figure 6:
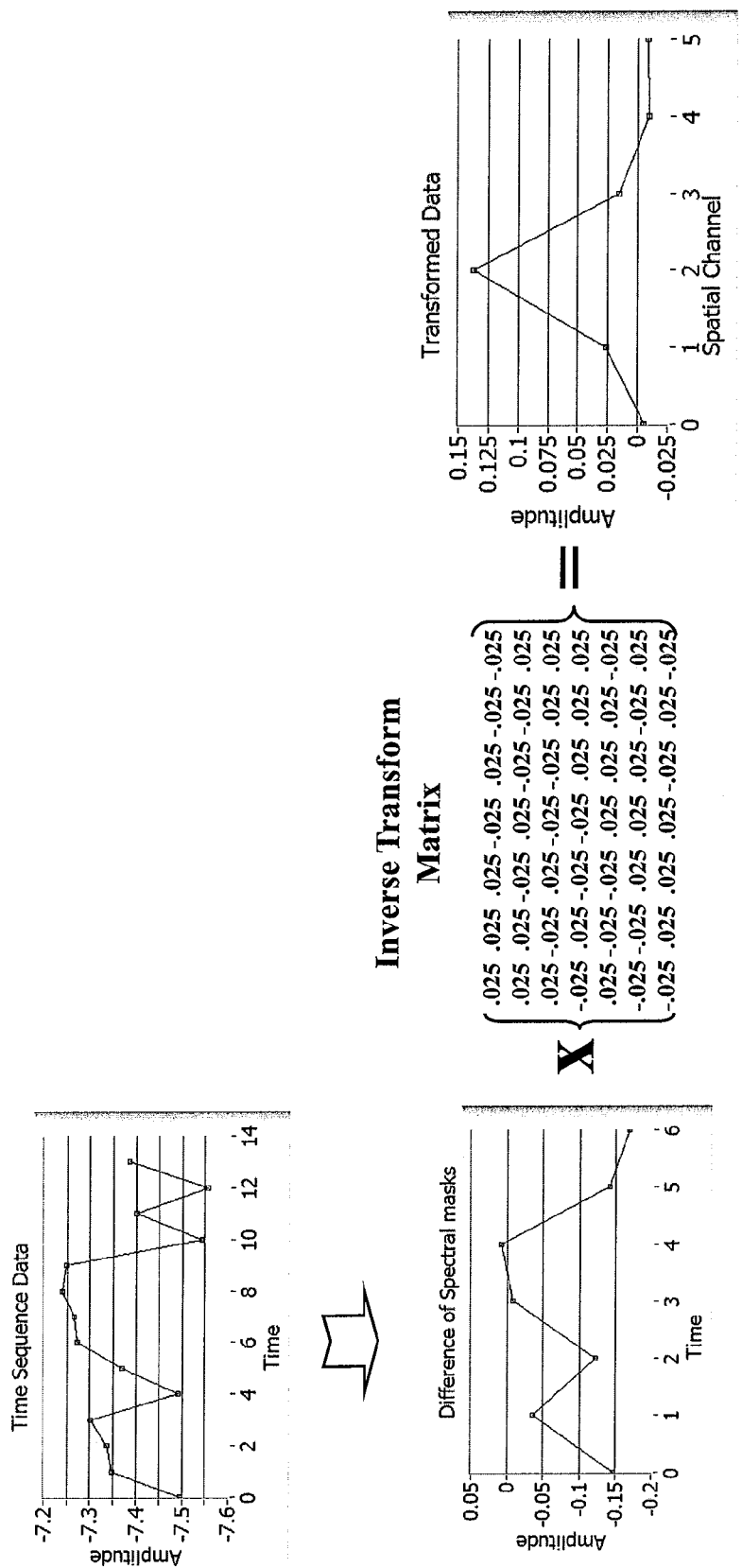
FIG. 6 shows a process of reconstructing spectral imagery from data formed through a sequence of spatially and spectrally encoded masks according to an embodiment of the invention.

FIGS. 5A, 5B and 6 illustrate the process for producing a one-dimensional spatial image with a spectral contrast signal based on the application of an analog spectral filter, while spatial multiplexing is used to maximize signal throughput.

FIGS. 5A and 5B illustrate the process of defining spatial masks to be applied to the SLM. In this case the process has three steps. First, define the set of superpixels that represent the portion of the dispersed image to be resolved. In this case, this set corresponds to 6 spatial channels and 16 spectral channels. The superpixels are organized into an ordered spatial scan along the slit direction using binary 'on' superpixels to pass the spectrum at each spatial position. This set of simple masks are shown on the left side of FIG. 5A.

Second, apply a linear transform to the set of spatial masks to produce a sequence of masks encoded to take advantage of the multiplexing of transform spectroscopy. The application of the transform is a well-known means for enhancing the signal collection in a multiplexed system. It is taught by Goldstein et al. and others. In this case, the transform is a Hadamard transform, using a cyclic simplex. The set of the transformed spatial masks shown on the right side of FIG. 5A contains the same spatial information as the original sequence, but each mask passes a larger fraction of light. The original sequence can be regenerated using the inverse transform.

Third, spectrally encode the masks by applying a set of analog grayscale masks to each spatial mask to discriminate the spectral transmission properties of each spatial position. This is shown in FIG. 5B. The resulting set of grayscale masks are used to detect the spectral contrast signal corresponding to a property of the target. In this case, apply a generalized version of a matched filter using a set of two masks. The matched filter is an analog spectral filter with positive- and negative-going components that is used to distinguish a target spectrum from a set of background interference spectra. The matched filter is represented by two analog grayscale masks to represent the positive- and negative going portions of a matched filter. Each mask is a spectral filter that defines the instantaneous spectral transmission function of the system. The trace in FIG. 5B shows the intensity profile applied to each of the rows of the mask.

The application of the spatially and spectrally encoded masks described above to an incoming signal is illustrated in FIG. 6. The system cycles through the series of masks in the spatial sequence that contains alternating positive and negative spectral templates. The time sequence data is collected, and the spectral contrast is computed by subtracting the amplitude of the alternating masks to yield the spectral contrast signal for each spatial mask. The data is then transformed, using the inverse of the transform that was used to create the spatial masks. Formally this is done by taking the cross product of the spectral contrast vector with the inverse of the transform matrix. The resulting transformed data is a one-dimensional spatial image of the spectral contrast at each spatial position.

The above is one example of how time domain multiplexing using encoded masks can be used to reconstruct spectral contrast signals. Other examples will be apparent to those skilled in the art. For example, the use of the transform in the second step is not necessary. The system could be operated as a spatially scanning system without transforms. The order of steps two and three can be reversed, with the transform being performed on the individual spectral filters. A set of grayscale masks could be applied to the spatial dimension to search for specific spatially distinct features in the image and form a spatial contrast spectrum.

Figure 7:
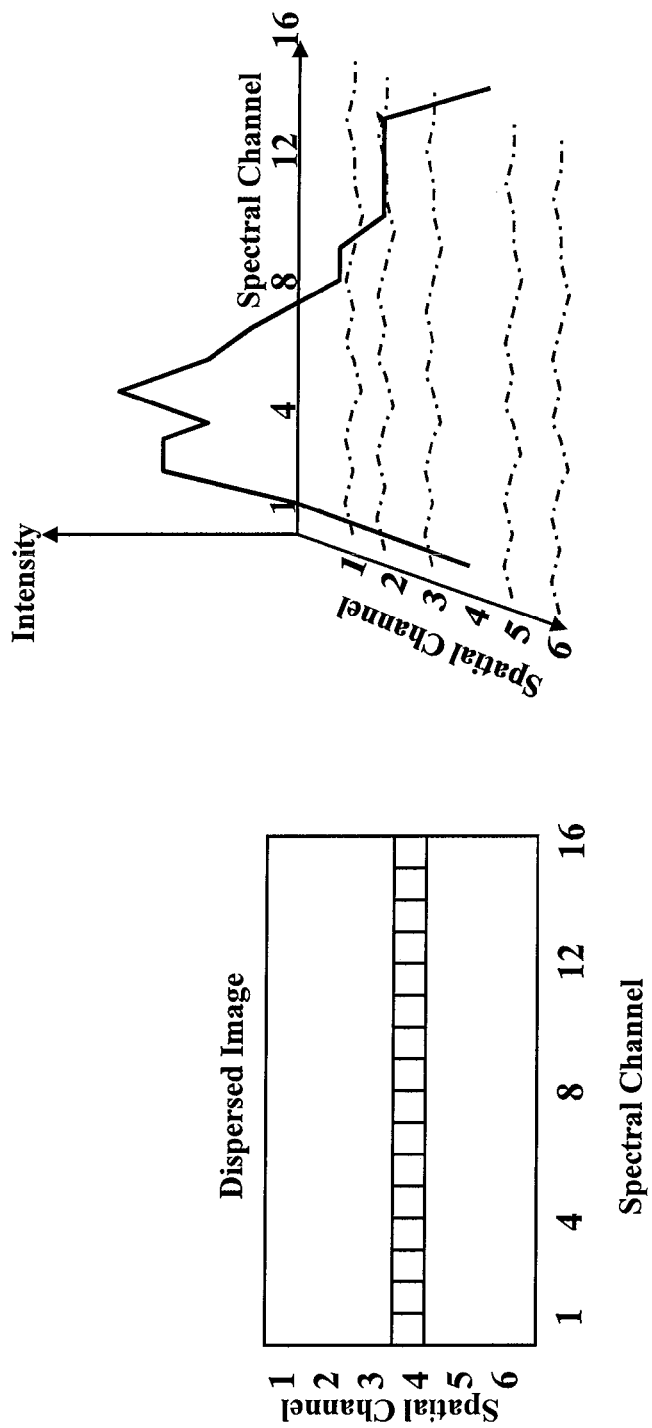
FIG. 7 shows a reconstructed hyperspectral image and corresponding spectral slices according to an embodiment of the invention.
Figure 8:
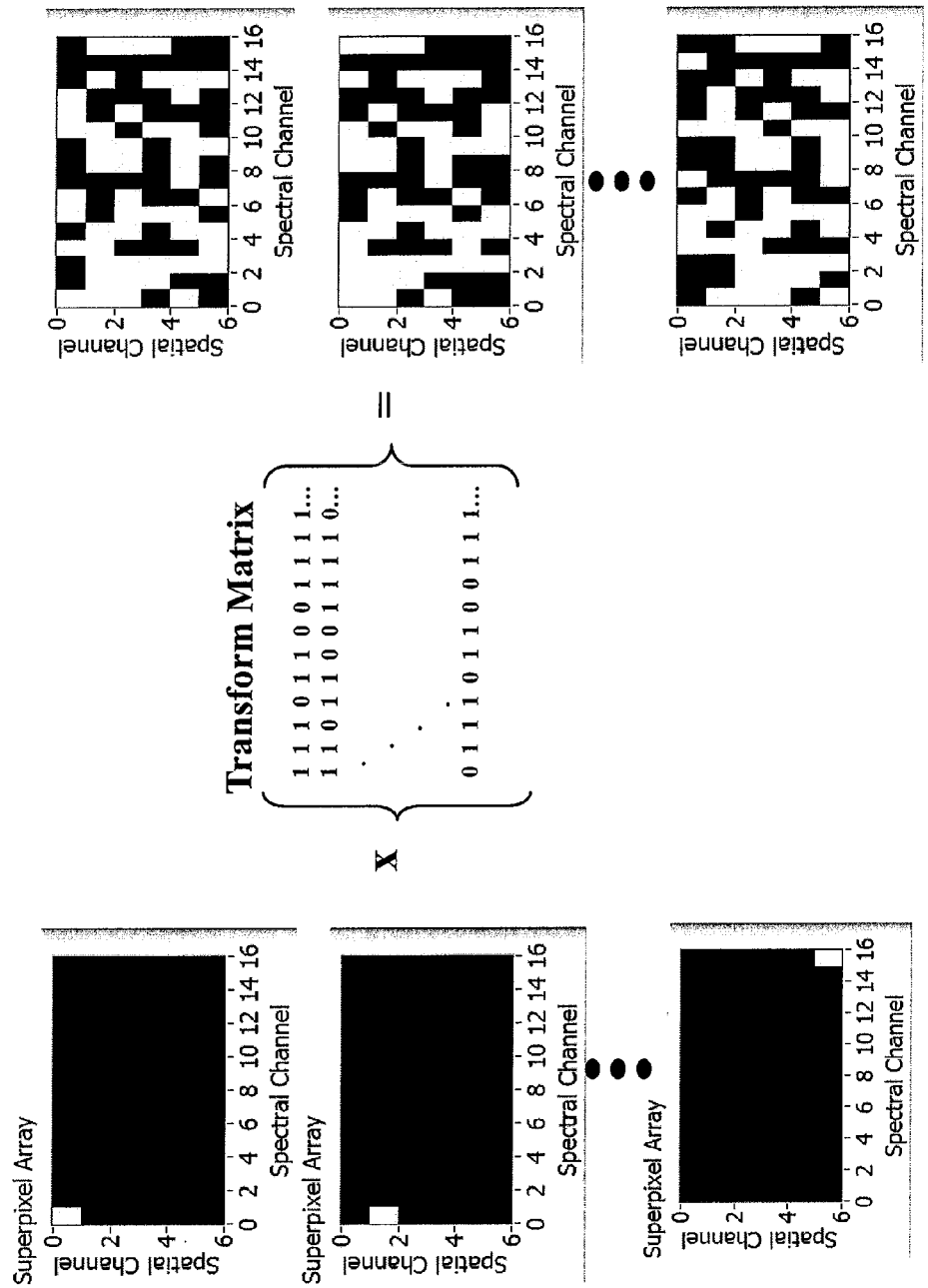
FIG. 8 shows a frame sequence in a superpixel basis according to an embodiment of the invention.
Figure 9:
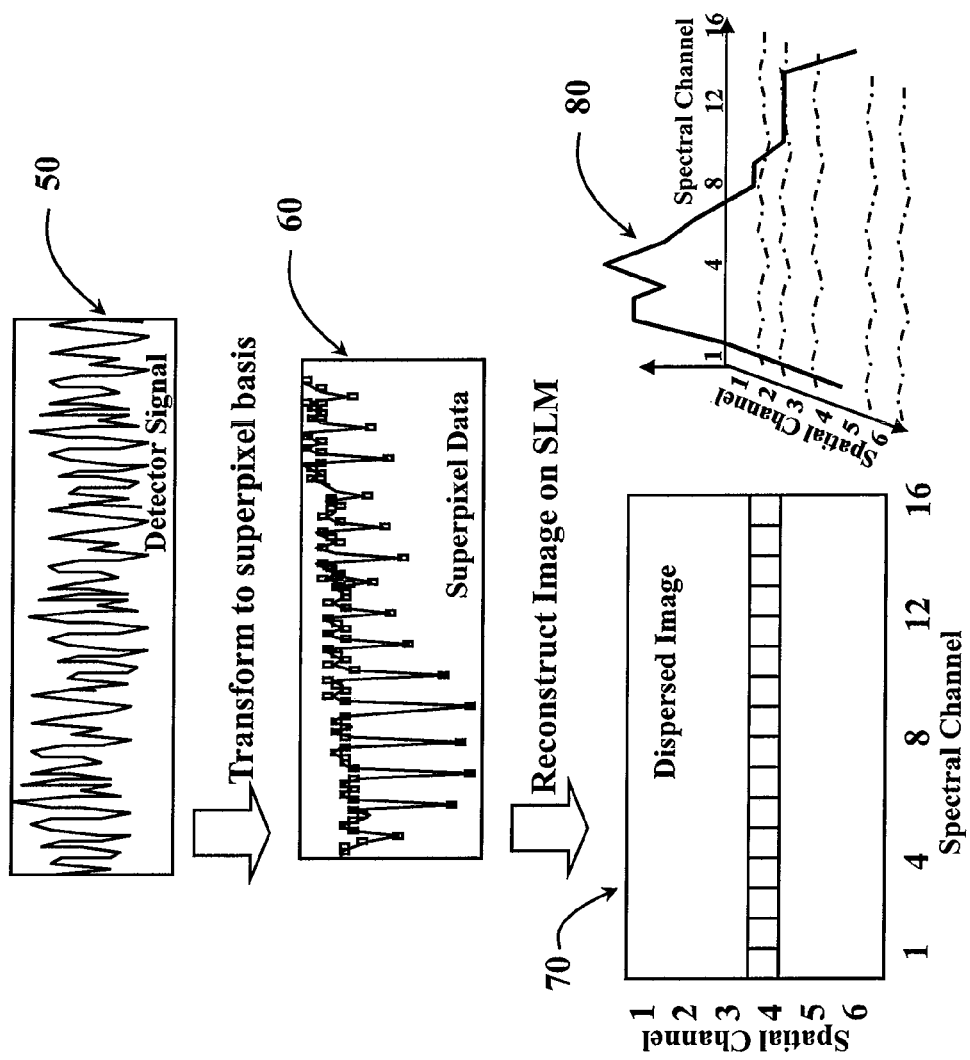
FIG. 9 shows a process of reconstructing a hyperspectral image according to an embodiment of the invention.

Other data products, such as spectrally resolved hyperspectral images can also be produced. FIGS. 7-9 illustrate a similar process for hyperspectral image generation. FIG. 7 shows a reconstruction of a two-dimensional hyperspectral image on the DMD face. A distant hot blackbody was focused on a pinhole near the input slit, creating a stripe of dispersed light on the DMD. The DMD area is divided into 6 spatial regions, and 16 spectral regions. These regions are defined by a 6×16 array of superpixels, where each superpixel consists of many DMD mirrors. The intensity trace in FIG. 7 depicts the intensity observed in each row, which corresponds to the spectrum of each spatially resolved element.

FIG. 8 illustrates the steps in making a spectrally encoded mask. In this case, a Hadamard Simplex transform of a superpixel-by-superpixel scan was implemented. In the first step, a set of frames is constructed corresponding to scanning a single superpixel stepwise though all 96 superpixels of a 6×16 array of superpixels. The frame sequence is padded with blank frames to bring the total number of frames up to 103, which is a number that can be transformed with the Hadamard Simplex transform. The frames are then transformed to produce a series of frames, each with approximately half of the pixels turned on. FIG. 8 shows a portion of the 103×103 cyclic S matrix used to transform the frames. The transformed frames are a linear combination of the input frames, where the frames are added according to the cross product of the frame index with the cyclic S matrix. Once the frame sequence is built in the superpixel basis, the frames are expanded to the DMD basis by turning on all DMD pixels belonging to active superpixels.

The reconstruction of the image is illustrated in FIG. 9. The raw detector data measures the intensity of the light transmitted by each of the Hadamard mask frames (0-103). The data is transformed to the original frame sequence by applying the Inverse S matrix to the input data. (Take the cross product of the signal with the inverse of the cyclic S matrix.) This signal is then mapped back to the image based on the original frame pattern sequence. In the example of FIG. 9, the hot blackbody illuminates row 4, and the detector response 50 results in a negative signal each time an element of row 4 is turned on. The transformed data, shown in the middle trace 60 of FIG. 9, has a periodic pulse every sixth frame, corresponding to the elements of the fourth row. The reconstructed image 70 shows an illuminated horizontal stripe across row 4, corresponding to the spectrum of the hot blackbody as shown in the intensity trace 80 through row 4. The intensity observed in each column corresponds to the intensity at a specific wavelength.

Preferred Embodiments of Spectral Filter Method for Producing Spectral Contrast

The above described how a set of spatial filters are used to develop spectral contrast imagery. This section discusses different embodiments of spectral filters that may be used for specific detection applications.

The spectral filter is used to tailor the spectral pass band of the adaptive spectral imager. The signal detected at the detector is the projection of the spectral filter function on the input radiance spectrum. The adaptive spectral imager is used in one of at least three different ways: 1) to constantly monitor the scene using a single spectral filter that emphasizes a property of interest, 2) to cycle through a small number of spectral filters of interest and compare the results, or 3) cycle through a set of spectral filters that span the spectrum of interest and generate a spectrum based on a linear combination of the measured results.

In a preferred embodiment, the spectral contrast image is produced by cycling through a sequence of two or more spectral filters, and performing linear operations on the measured projection data to produce a spectral contrast image that is characteristic of the physical properties of the targets within the scene. The spectral filters are adapted to the requirements of sensing the target with a particular scene, and thus are dependent on the detailed spectral structure of the target, the detailed spectral structure of the background, and the instrument noise associated with the measurement. Spectral filters can be calculated in real time and updated to reflect changes in any of the above properties.

The physical properties to be observed can include detection of the target based on a characteristic spectral feature, or detection of a characteristic physical property of the target, such as temperature or composition ratio through comparison of two or more spectral features. The scene background may also have a detailed structure, which can vary among elements of the scene. In addition, the filters need to discriminate against instrument noise that may be uncorrelated with the spectral content of the scene.

In traditional, non-adaptive target detection algorithms, complete spectra are recorded for each spatial element, and then these spectra are processed to detect a property of the target using a set of linear operations on the detected spectral channels. With the adaptive spectral imager, data are recorded for a smaller number of complex spectral filters, each of which is a combination of different spectral channels.

Any target detection technique that is based on a linear combination of spectral channels can be implemented using the adaptive spectral imager. These include techniques such as a simple static spectral filter, matched filters, sub-space projection, multivariate regression vectors leading to principal component analysis, end member generation algorithms, genetic algorithms, Hadamard masks for spectral multiplexing, masks for derivative modulation of the spectrum, and various combinations thereof.

Any and all of these approaches can be improved by the realization that instrument noise propagates differently in the adaptive spectral imager than it does when a standard imaging spectrograph is used. For spectrograph systems that collect the full spectrum, all spectral channels are recorded with a common probability of instrument noise. The spectral filter constructed from a linear combination of measured spectra thus contains an accumulation of instrument noise that has the same linear transformation as the signal. For an adaptive spectral imager, the instrument noise is associated with the single measurement of the spectral filter, and is independent of the details of the spectral filter. Thus, a detection algorithm such as a matched filter, that is optimal for processing spectra, may be sub-optimal for detection using complex spectral filters in the adaptive spectral imager, and can be improved by explicit consideration of the noise propagation.

Implementation of extended matched filters

Considered here is an embodiment of an extended matched filter as an example of an implementation of a linear detection algorithm in the adaptive spectral imager. A matched filter is an analog filter function used to detect a target spectrum in the presence of structured background spectra. The target is detected by taking the dot product of the observed spectra with the matched filter.

Matched Filter Definition

For a "target" with a known spectrum embedded in a scene with a variable background, perhaps the most popular method for detection is matched filtering, which is a mean-subtracted variant of Constrained Energy Minimization filtering (CEM). This method is commonly used to sensitively detect and locate a gas cloud in spectra acquired by remote sensors. The matched filter approach enables sensitive detection of a feature in either absorption or emission, although it does not necessarily yield a quantitative measure of concentration due to the ambiguity between transmittance and temperature.

The matched filter q is a linear filter vector, i.e., a spectrum whose inner product with the measured spectrum p extracts a target amplitude (or "abundance") estimate:

$$\text{Amplitude} = q^T p \quad (1)$$

Here $^T$ denotes the array transpose and the data p are mean-subtracted. q is derived from the maximum likelihood estimate for the target abundance assuming an additive Gaussian "noise" background. This background, which incorporates all sources of variability such as detector noise and scene radiance clutter, is assumed to be described by second-order statistics, i.e., a covariance matrix C and a mean value. The covariance is best estimated from spectral data for the scene, such as from the pixels of a spectral image or, for a non-imaging sensor, from sequential spectral observations.

The standard matched filter or CEM filter, is the filter that maximizes the signal to noise ratio for detection of the target in the presence of the Gaussian background (with no additional detector noise). The analytical expression for the standard matched filter is:

$$q = C^{-1} t / [t^T C^{-1} t] \quad (2)$$

where t is the mean-subtracted target spectrum. The normalization factor, $[t^T C^{-1} t]$, is arbitrarily chosen to yield a value of one for detection of the target spectrum. For a cloud target, t may be taken as differential radiance due to the target absorption and emission.

In the adaptive spectral imager, the matched filter is implemented in hardware by adjusting the transmission of each superpixel. With unit transmission, the instrument measures the spectrum p. Grayscales are used to attenuate the transmission of specific spectral channels to achieve an arbitrary spectral transmission function. The matched filter, $q^T$, is constructed using a set of grayscales, one grayscale, $q^{T+}$, is used to represent the positive-going portion of the filter and a second, $q^{T-}$, is used to represent the negative-going portion of the filter.

$$q^T = q^{T+} + q^{T-} \quad (3)$$

$$\text{Amplitude} = q^{T+} p - q^{T-} p \quad (4)$$

The two grayscales are applied in rapid succession, and the two amplitudes are subtracted to yield the matched filter amplitude, Amplitude=$q^T p$. This process is illustrated below.

Extension to an Ideal Filter for Adaptive Sensing

The idea of the matched filter can be generalized to cases with an additive instrument noise as follows. The objective is to define a linear filter, i.e., a pair of frame response functions that maximizes the total signal-to-noise, where the noise includes both the background and the instrument component. Let N be the number of spectral channels. Let t be the signal spectrum to be detected (dimension N), C the background covariance matrix (dimension N×N), h be the desired filter spectrum (dimension N, positive values being assigned to the first frame and negative values being assigned to the second frame), and n the instrument noise (scalar) during the two frames. Then the squared signal-to-noise ratio is written as $$\text{SNR} = h^T t t^T h / (h^T C h + n^2) \quad (5)$$

This quantity is to be maximized.

In the limit n=0 an analytical solution, the CEM filter, exists for a given normalization of h; it is equivalent to the matched filter, q, when the data are mean-subtracted. The same solution would apply for finite noise if the magnitude of the background term, h, were arbitrarily large compared to the magnitude of the read noise.

Figure 10A:
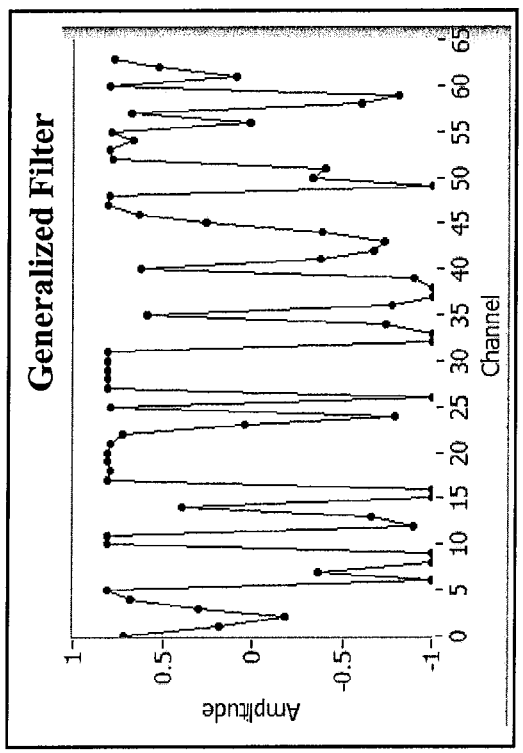
FIGS. 10A and 10B illustrate a comparison of the generalized filter and matched filter for one embodiment of the invention.
Figure 10B:
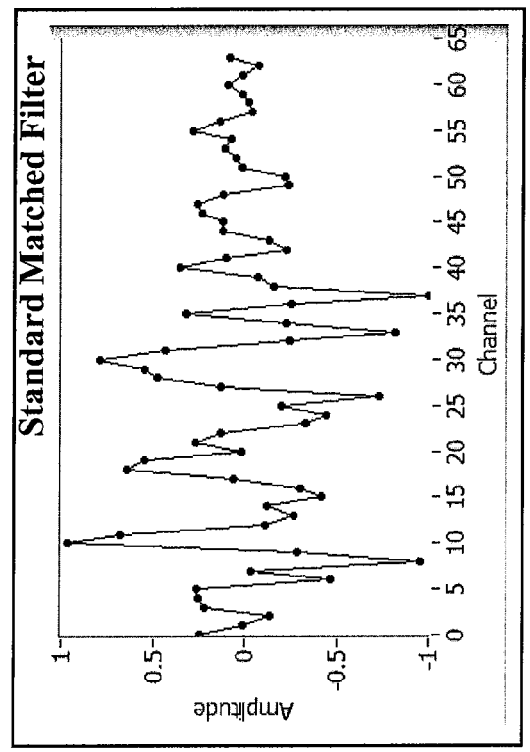
Figure 11:
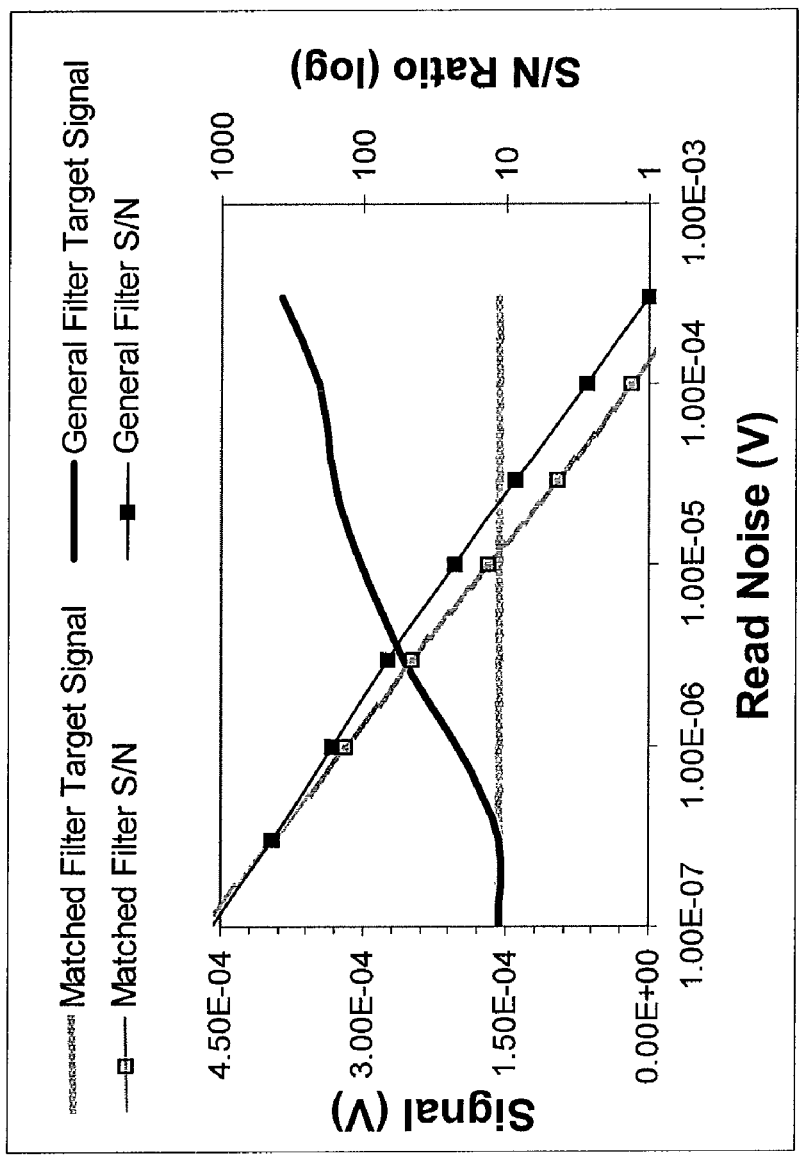
FIG. 11 shows the dependence of signal and noise on the relative size of the read noise versus background according to an embodiment of the invention.

If the read noise is large compared to the structured background signal variation, the background structure has little affect on the signal to noise ratio, and the optimum generalized filter is one that maximizes the total signal level, independent of the background. For cases where the detector noise and structured background are comparable, the optimum filter produces the largest signal without raising the contribution of the background above that of the read noise. FIGS. 10A and 10B compare the shape of the generalized filter from Eq. (5), FIG. 10A, to that of the CEM filter (matched filter), FIG. 10B for detection of the polystyrene spectrum in the 7-13 micron spectral region in the presence of blackbody backgrounds. In this case the read noise is larger than the structured background, $n=50 (h^T R h)^{1/2}$. Since the detector noise is greater than the background contribution, the optimum generalized filter is one that transmits more of the target spectrum, thereby producing a larger signal, with only a marginal impact on the total noise. FIG. 11 shows the systematic variation in the signal and the signal to noise ratio as a function of the relative size of the readout noise. For practical applications in the LWIR, the read noise is usually one to two orders of magnitude larger than the residual background signals of a CEM filter, and the signal-to-noise ratio is 2-3 times better with this generalized filter than with the CEM filter.

In many applications of the adaptive spectral imager, the instrument noise term is considerable, and the optimum filter for detection of the target differs from the standard matched filter. The ideal filter is dependent on the relative magnitude of the instrument noise, n, and the scene covariance, C. The ideal filter can be calculated dynamically during instrument operation, given the values for these two parameters.

The adaptive spectral imager can update the ideal spectral filters based upon any source of data. It can use external data about the scene, such as location, time of day, process conditions, etc. to compute the appropriate covariance matrix for the scene, or it can rely on stored values of measurements of the scene or cataloged background spectra.

Other detection methods can also be generalized in a similar manner to take account of the unique noise propagation inherent in the adaptive spectral imager approach. The decoupling of the instrument noise from the spectral resolution changes the optimal detection strategy for all detection and quantization schemes based on linear filter projections in a similar manner to that outlined above for the specific case of the CEM filter.

Projection Methods

The adaptive spectral imager records the projection of the spectral filter onto the radiance spectrum of the scene. In other words, the detector measures the inner (dot) product of the spectral filter with the scene spectrum. Thus, the adaptive spectral imager can be used with any detection method that is based on projection operators.

In process monitoring applications and other applications, the spectral filters can be optimized to measure a specific set of spectral features that represent physical properties of the target. In many applications, such as combustion monitoring, the spectral properties of the target and background are known, and can be described by a small number of complex spectra that span the space of high-resolution spectra observable in the scene. For example, the spectrum of a flame is dominated by the emission of specific emitters such as water, $CO_2$ and soot that have a well-defined, temperature dependent spectrum. A small number of spectral functions can completely describe the temperature and composition of the flame. Goldstein et al. (US Pat. No. 6,640,199) teach a method of measuring temperature or composition based on taking the projection of the spectrum onto two spectral functions and taking the ratio of two projections. Any such processing can be done in real time using the adaptive spectral imager. Two or more spectra are applied as spectral filters to the adaptive spectral imager, and the resulting signals are compared to produce an indicator of temperature or composition. The spectral filters used to extract physical information need not be orthogonal. Any set of spectra that differentiate a physical property may be used.

In one embodiment, only a single projection operator (a single spectral filter) is used to monitor the concentration of a specific target. For example, in a combustion monitor we can track the time evolution of an exhaust product such as $H_2O$ by monitoring the time evolution of detected radiation within its characteristic spectral band. The adaptive spectral sensor can act in a staring mode, collecting time resolved data through a single mask, or may use alternating masks, while collecting time-resolved information during the duration of each individual mask.

In a second embodiment, the system can cycle through two or more spectral filters and linear combinations of the projected intensities can be used to measure quantities of interest. For example, we can measure the ratio of intensities of two spectra to determine the ratio of concentrations of $H_2O$ and $CO_2$, which determines the completeness of combustion.

In a third embodiment, the system can use spatial multiplexing and multiple detector elements to measure two or more spectral bands simultaneously.

In a fourth embodiment, the system can combine multiple spectral filters to detect and quantify the target species in the presence of a background emitter. This can be done using a set of orthogonal projections that span the subspace of interest, or using a set of filters that take into account the covariance of the background spectra in a manner analogous to the matched filter approach.

Spectral Scans

In one method of operation, the applied spectral filters are part of an orthogonal set of spectral basis functions that completely describe the spectrum of the scene as observed over a defined spectral interval with a defined spectral resolution. If the spectral filters are orthogonal, the complete spectrum can be recorded by cycling through the orthogonal set of spectra. In practice, it is only necessary to measure a subset of the orthogonal basis spectra that is of interest in computing the physical property of interest. Often, the set of spectral filters can be truncated at a small number.

The orthogonal set of spectra may be a general set such as the cyclic simplex and Hadamard matrices that are used to efficiently record complete spectra at uniform resolution. However, it is not necessary to restrict operation to spectra obtained with uniform resolution. Spectral elements can be grouped together to form spectral basis functions with local resolution that is optimized for the detection of specific spectral features. For example in scenes that are dominated by emission from sources with complicated spectral features, an orthogonal basis of complex spectra that span the sub-space of all known spectral features can be used.

In many instances, such as process monitoring, a set of a dozen or fewer spectra can completely describe the full set of high-resolution spectra that can be observed in the process environment. Therefore, instead of making high-resolution spectral scans with hundreds or thousands of spectral resolution elements, the spectra can be described in a much smaller basis of component spectra. Often, the concentration of one species can be detected based on the projection of a single characteristic basis function on the scene. Often, a number of emitting species can be detected and quantized using a similar number of spectral basis functions. These component spectra can be applied to the adaptive spectral imager as spectral filters.

Use of such tailored spectral basis functions not only reduces the number of spectral measurements that must be collected, but optimizes the signal to noise ratio for the collected spectra. Since the noise level is determined by the detector, and decoupled from the spectral resolution, the use of highly structured spectral basis functions allows the detection of high-resolution spectral information using a small number of measurements, thereby optimizing the detection sensitivity.

Derivative Spectroscopy

The adaptive imager can be used to record directly the derivative spectrum of a scene of interest by alternating spectral filters with small shifts in frequency in the vicinity of spectral features of interest. This approach is useful in differentiating the spectral contributions from sharp spectral features from those features with smoothly varying spectra. It is also useful for rejecting background contributions from noise—rich frequency bands (usually at the low frequencies). The technique offers improved dynamic range and improved sensitivity relative to existing multispectral and hyperspectral instruments. Derivative detection can be applied in conjunction with any of the above-mentioned detection techniques.

Derivative spectra can be recorded by alternating members of two sets of measurements, one set that records a subset of spectral bands, and a second set that records a second set of bands with a small wavelength shift relative to the first. The two sets are alternated and the difference taken to produce the finite differential spectrum with respect to wavelength. Derivative spectra of arbitrary order can be recorded using appropriate waveforms.

Although specific features of the invention are shown in some drawings and not others, this is for convenience only as some feature may be combined with any or all of the other features in accordance with the invention.

Other embodiments will occur to those skilled in the art and are within the following claims.

What is claimed is:

1. A method of detecting specific properties of a radiance image of a scene in hardware using a spectrally encoding sensor system comprising: a spectrograph that forms a dispersed image comprising multiple spectral components displaced along a dispersion direction; a programmable spatial mask for encoding filter functions on the dispersed image where the filter functions select specific spectral pass bands and/or spatial locations; and optical elements that direct the encoded dispersed radiation onto a detector that records the intensity transmitted through each mask, the method comprising:

successively encoding a series of two or more filter functions with the programmable spatial mask, to make two or more successive measurements that each measure the inner product of the filter function with the scene radiance spectrum, where the filter function contains a combination of spectral pass bands that emphasize one or more specific properties of a target or analyte that may be located within the scene; and comparing two or more measurements using linear operations such as subtraction and ratios, to produce a contrast signal indicative of the specific properties of the scene.

2. The method of claim 1 where the filter functions are analog transmission functions that are implemented using gray-scales on the spatial mask.

3. The method of claim 2 where the grayscales are implemented using variable on and off times for the individual mirrors.

4. The method of claim 2 where two or more of analog transmission functions are used to implement a generalized version of a matched filter, or other detection methods based on linear projection operations, which optimizes signal to noise ratio in the presence of constant detector read noise.

5. The method of claim 2 where the analog transmission functions are used to project the radiance spectrum onto a set of spectral basis functions representative of materials and conditions in the scene.

6. The method of claim 1 where the filter functions are adaptive filter functions that emphasize a known and pre-selected target spectrum while minimizing the response to other known spectral features within the scene.

7. The method of claim 1 further comprising automatically, dynamically adjusting the filter functions to reflect changes in the background spectral features within the scene.

8. The method of claim 7 further comprising collecting detailed spectral scans of the scene to determine the spectral features of the background scene.

9. The method of claim 8 further comprising updating the optimal filter functions for detection based on a spectral data recorded previously for the specific scene.

10. The method of claim 8 further comprising updating the optimal filter functions for detection based on the most recent spectral data collected over a range of viewing or operating conditions.

11. The method of claim 7 where the adjustment is based on knowledge of the general scene conditions.

12. The method of claim 1 where the specific property comprises a concentration, temperature, or other physical property of a specific analyte within the scene.

13. The method of claim 12 where the specific property comprises the relative values of the physical properties of two or more analytes.

14. The method of claim 12 where the monitored scene is part of a process or system with a well defined range of possible spectral characteristics that depend on the state of the system or process.

15. The method of claim 14 where the process involves hot combustion products and the physical properties include temperature, concentrations, or dynamic fluctuations of combustion products.

16. The method of claim 12 further comprising recording the physical property as a function of time to determine the dynamic behavior of the system.

17. The method of claim 12 where the physical property is measured at a specific location within the field of view of the sensor.

18. The method of claim 12 further comprising using fiber-optics to direct radiation from a specific location to the sensor system.

19. The method of claim 1 further comprising producing a control signal, proportional to the contrast signal, that is used to initiate a physical action that affects the specific property.

20. The method of claim 1 where the filter function is selected to produce the derivative of the target or analyte spectrum.

21. The method of claim 1 where the spatial light modulator is a digital micromirror array and the basic resolution unit is a superpixel consisting of multiple individual mirrors and where the spectral and spatial resolution of the measurement can be adjusted by changing the size and shape of the superpixel.

22. The method of claim 21 where grayscales are implemented by activating a fraction of the individual mirrors within the superpixel element.

23. The method of claim 1 further comprising recording the transmitted intensity through at least one spatial mask as a function of time to determine the dynamic behavior of the system.

24. The method of claim 1 wherein a filter function comprises a spatial filter function to resolve spatial structure in the image.

25. The method of claim 1 further comprising a set of spectral filter functions that resolve the spectral information in the scene using a reduced number of spectral filters relative to a full spectral scan at constant resolution.

26. A method of detecting specific properties of a radiance image of a scene in hardware using a spectrally encoding sensor system comprising: a spectrograph that forms a dispersed image comprising multiple spectral components displaced along a dispersion direction; a programmable spatial mask for encoding filter functions on the dispersed image where the filter functions select specific spectral pass bands and/or spatial locations; and optical elements that direct the encoded dispersed radiation onto a detector that records the intensity transmitted through each mask, the method comprising:

applying information about the range of possible spectral features in the scene to develop a set of spectral filter functions that provide a near-complete description of all possible spectral features in the scene and allow the detection of high-resolution spectral information using a small number of measurements, the spectral filter functions designed for the detection of specific physical properties in the scene;

encoding one or more spectral basis functions with the programmable spatial mask, to measure the inner product of the filter function with the scene radiance spectrum; and producing a signal indicative of the specific physical property in the scene.

27. The method of claim 26 in which a spectrum of the scene is measured by sequentially applying members of the set and comparing the measurements.

28. The method of claim 26 further comprising comparing two or more measurements using linear operations such as subtraction and ratios, to produce a contrast signal indicative of the specific properties of the scene.

29. A method of detecting specific properties of a radiance image of a scene in hardware using a spectrally encoding sensor system comprising: a spectrograph that forms a dispersed image comprising multiple spectral components displaced along a dispersion direction; a programmable spatial mask for encoding filter functions on the dispersed image, where light from a single spatial element is directed to two or more distinct areas of the spatial mask, and where the filter functions select specific spectral pass bands; and optical elements that direct the encoded dispersed radiation onto a detector array that records the intensity transmitted through each distinct area of the spatial mask, the method comprising:

encoding two or more filter functions with the programmable spatial mask, to make two or more simultaneous measurements that each measure the inner product of a filter function with the radiance spectrum of the spatial element of the scene, where the filter functions each contain a combination of spectral pass bands that emphasize one or more specific properties of a target or analyte that may be located within the scene; and comparing two or more measurements using linear operations such as subtraction and ratios, to produce a contrast signal indicative of the specific properties of the scene.

\* \* \* \* \*